United States Patent
Nicholas

(10) Patent No.: US 6,538,727 B2
(45) Date of Patent: Mar. 25, 2003

(54) ELECTRONIC DEVICE FOR DISTINGUISHING SUGAR SWEETENED BEVERAGES FROM ARTIFICIALLY SWEETENED ONES

(76) Inventor: Paul H. Nicholas, 640 S. Griffith Park Dr., Burbank, CA (US) 91506

( * ) Notice: Subject to any disclaimer, the term of this patent is extended or adjusted under 35 U.S.C. 154(b) by 36 days.

(21) Appl. No.: 09/836,820

(22) Filed: Apr. 17, 2001

(65) Prior Publication Data

US 2001/0035950 A1 Nov. 1, 2001

Related U.S. Application Data

(60) Provisional application No. 60/197,898, filed on Apr. 17, 2000.

(51) Int. Cl.$^7$ ................................................ G01N 21/41
(52) U.S. Cl. ........................................ 356/136; 356/133
(58) Field of Search ................................ 356/128, 135, 356/136, 137, 133, 134; 250/301

(56) References Cited

U.S. PATENT DOCUMENTS

| | | | | |
|---|---|---|---|---|
| 3,751,168 A | * | 8/1973 | Liop et al. | 356/135 |
| 4,306,805 A | * | 12/1981 | Arrington | 356/133 |
| 4,320,291 A | * | 3/1982 | Uramoto | 356/136 |
| 4,699,511 A | * | 10/1987 | Seaver | 356/136 |
| 5,859,696 A | * | 1/1999 | Nicholas et al. | 356/128 |

* cited by examiner

Primary Examiner—Huy Mai
(74) Attorney, Agent, or Firm—Edgar W. Averill, Jr.

(57) ABSTRACT

A refractometer which provides a "sugar" or "diet" indication when immersed on a beverage. The device is electronic and lights either a "sugar" or "diet" signal to the user. A prove has a light source and a photodetector at one end and an angled face at the other end. Depending on the refractive index of the beverage, the light is either reflected back into the probe and into the photodetector and exits out of the angled face and does not reflect back to the photodetector.

13 Claims, 4 Drawing Sheets

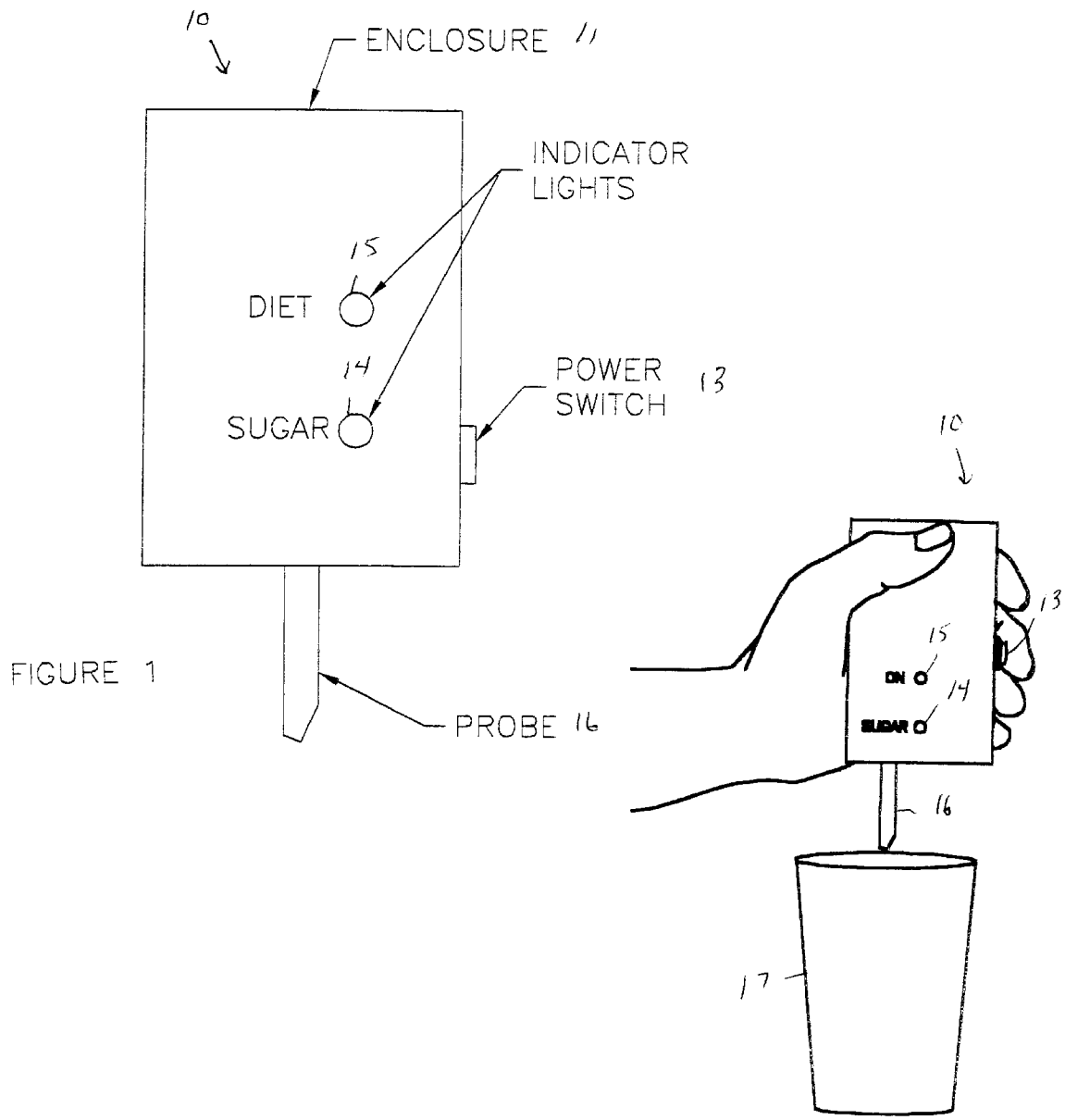

ELECTRONIC DEVICE FOR DISTINGUISHING SUGAR SWEETENED BEVERAGES FROM ARTIFICIALLY SWEETENED ONES

This is a nonprovisional application of provisional patent application Serial No. 60/197,898 filed Apr. 17, 2000.

BACKGROUND OF THE INVENTION

This invention is a device to be used for determining whether a beverage is of the artificially sweetened "diet" variety or the sugar sweetened variety. This is useful for beverages, such as carbonated soft drinks, which are sold in both varieties, the two being almost identical in taste and appearance. Many people, such as diabetics or calorie-conscious dieters, could benefit from a simple, reliable means of differentiating between the two varieties.

This invention uses the index of refraction of the beverage to determine whether the beverage contains sugar. As the concentration of sugar in a beverage is increased, the index of retraction of the beverage increases as well. Because artificial sweeteners are only used in minute quantities in diet soft drinks, the refractive index of diet drinks is essentially the same as that of pure water. A typical sugar sweetened soft drink, on the other hand, contains enough sugar to make its refractive index considerably higher than that of its artificially sweetened counterpart.

The sugar sweetened versions of most soft drinks contain about 12% sugar by weight as they come from the bottle and may vary as low as 6% sugar after dilution by melted ice.

The device consists of a probe which is dipped into the beverage to be tested, together with electronic circuitry which determines the type of beverage being tested. The device turns on an indicator light to display the result of the test. The invention has advantages over devices such as that described in U.S. Pat. No. 5,859,696, "Refractometer for distinguishing sugar-sweetened beverages from artificially-sweetened ones", which require enough ambient light for the user to be able to see light passing through the liquid. This invention is easier to use because the user only needs to dip the probe in the beverage and press a button to perform a test. The test is also more discreet because the user does not need to raise the device to his eye. This invention has an advantage over chemical test strips which can only be used once and which have a limited shelf life. The device is only intended to indicate whether a beverage is of the diet or sugar-sweetened variety, rather than producing a high accuracy measurement of refractive index. Thus it can be simpler, more compact and more economical than devices which produce high accuracy measurements.

This device could be useful to those people who wish to avoid sugar because of diabetes, dental problems or weight control concerns. People with phenylketonuria (PKU) must avoid aspartame, a common artificial sweetener. Some people experience nervous system problems when they drink beverages containing aspartame and may wish to avoid diet soft drinks. Many people are wary of any possible long term health effects of consuming artificial sweeteners and want to avoid them to reduce their possible risk of cancer or other illnesses.

BRIEF DESCRIPTION OF THE DRAWINGS

FIG. 1 is a plan view of the device for distinguishing sugar sweetened beverages of the present invention.

FIG. 2 is a front view of the device of FIG. 1 shown being held over a container of a beverage.

DESCRIPTION OF THE PREFERRED EMBODIMENTS

Figure 3:
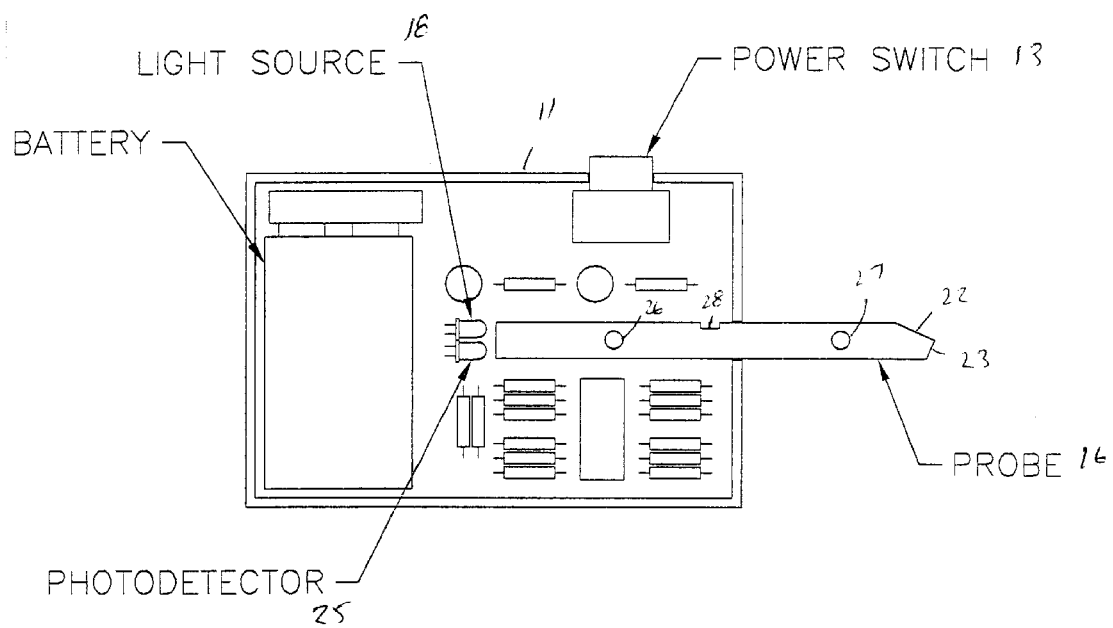
FIG. 3 is a cut-away view showing the internal elements of the device of FIG. 1.

In the preferred embodiment, the device 10 has an enclosure 11, shown in FIG. 1, which houses the electronics and a source of power, such as a battery 12 (shown in FIG. 3). The enclosure has a button 13 which the user presses to activate the device. The device has red 14 and green 15 indicator lights which display the results of the test being conducted. A probe 16 made from a transparent material such as glass or plastic projects from the enclosure.

FIG. 2 shows the device 10 being held over a container 17 of a beverage. The probe 16 is dipped into the beverage shortly after the power switch 13 is depressed. If the drink contains ice, the drink should be stirred with a straw or spoon to thoroughly mix in any water that may have formed as the ice melted (otherwise a false indication of "diet" could result).

The device should be held so the button can be pressed while the probe is dipped into the drink, and so the indicator lights can be seen. FIG. 2 shows a comfortable way of holding the device. Press the button so the "ON" light comes on. Firmly hold the button in and dip the probe quickly into the drink. It should be dipped in at least as far as to cover the tip of the probe. Watch the indicator lights as the probe goes into the drink. If the red "SUGAR" light comes on, the drink is of the "regular" type. If just the green "ON" light stays on, the drink is of the "diet" type. Carefully wipe the probe dry after using the device. Avoid smearing grease on the probe or scratching the shiny face at the end. If testing more than one drink, wipe excess beverage off the probe after testing each drink.

If the probe is held in the drink for more than a couple of seconds, and the drink is highly carbonated, the red light may go out and the green light come back on. This is due to bubbles covering the probe and preventing the liquid from touching the sensing area on the probe. This is why it is important to dip the probe in quickly and watch to see if the lights change.

The device should not be used to test for the presence of sugar in drinks that contain alcohol. Alcohol can produce the same indication as sugar, giving a false positive reading.

Figure 4:
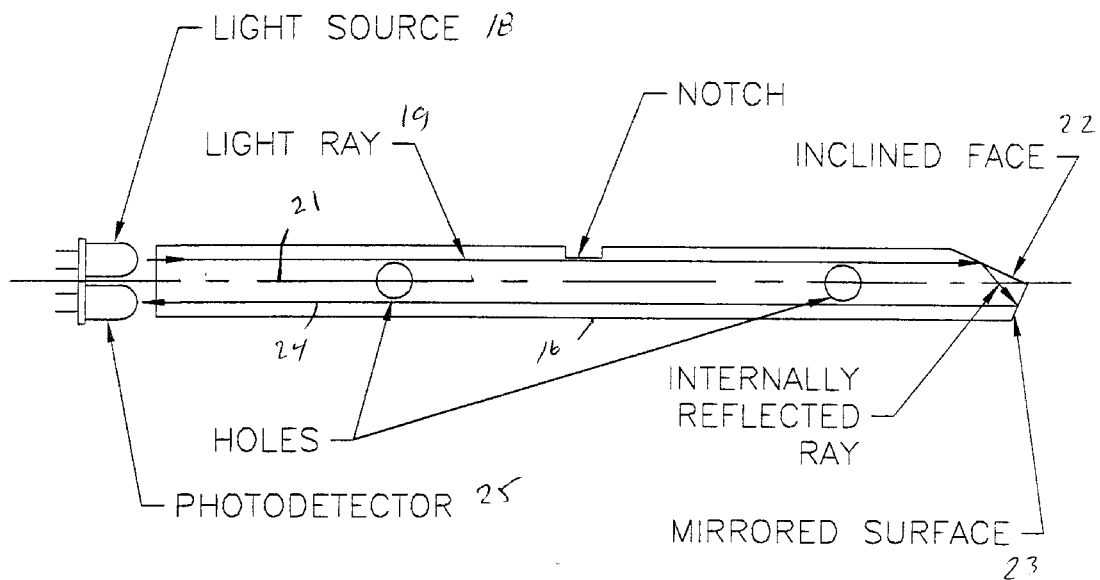
FIG. 4 is a cross-sectional side view of the probe, light source, and photodetector of the device of FIG. 1.

FIG. 3 shows a cut-away view of the preferred embodiment of the invention. A light source 18 inside the enclosure 11 is positioned so as to project a beam of light 19 into the light-receiving end 20 of the probe 16, as shown in FIG. 4. The light beam 19 travels parallel to the long axis 21 of the probe 16 and impinges on an inclined face 22 at the extreme end of the probe. Any light which is reflected from this face bounces to a mirrored surface 23 in the probe and is reflected back through the probe 16. The reflected ray is indicated in FIG. 4 by reference character 24. Ray 24 strikes a photodetector 25 inside the enclosure. The probe 16 has two holes 26 and 27 and a notch 28 positioned so as to prevent stray reflections and light from external sources from reaching the photodetector 25.

Figure 5:
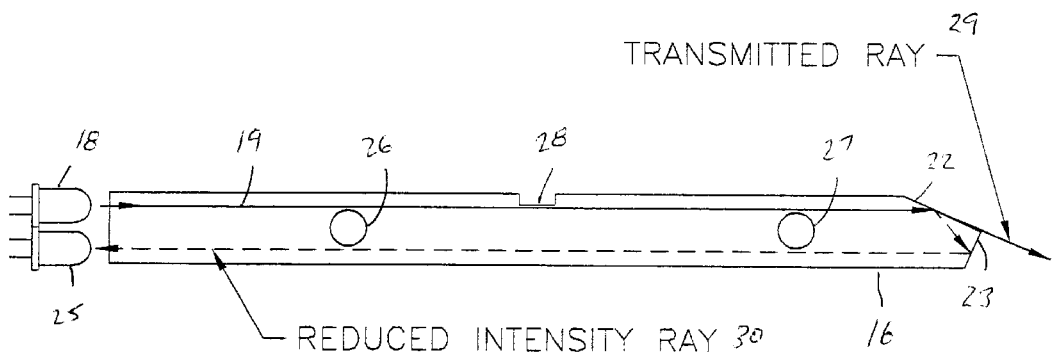
FIG. 5 is a cross-sectional view of the probe, light source, and photodetector of the device of FIG. 1.

The light beam 19 striking the inclined face 22 at the end of the probe is reflected from, or transmitted through, the face 22 to an extent which depends on the refractive index of the medium in contact with the face. The angle of the face is chosen so that the beam 19 is totally reflected when the index of refraction is equal to that of pure water or a diet beverage. When the index of refraction is that of a sugar sweetened beverage, a large portion of the light beam 19 is transmitted through the face into the beverage as shown in FIG. 5. The transmitted ray is indicated by reference character 29. As a result, the amount of light striking the photodetector drops. The lower intensity light ray 30 is an indication of a sugar-sweetened beverage.

Figure 6:
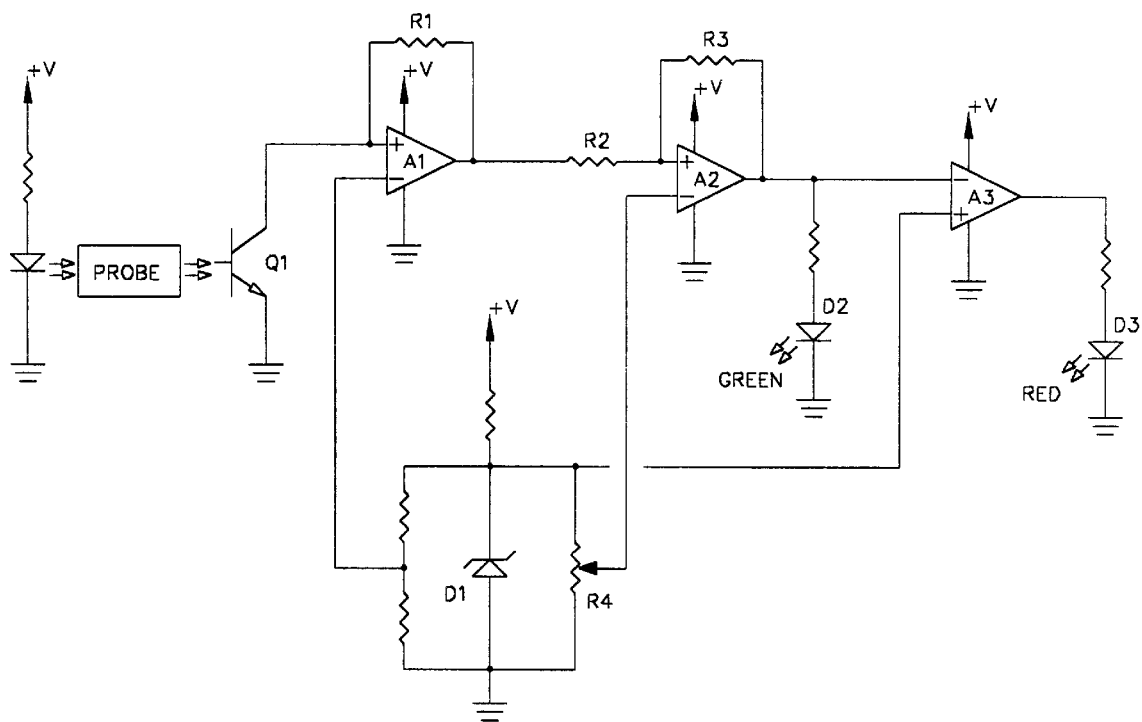
FIG. 6 is a circuit diagram of the device of FIG. 1.

An electronic circuit, shown in FIG. 6, is used to determine whether the light intensity striking the photodetector corresponds to a sugar-sweetened or a diet beverage. Amplifier A1 is used as a current-to-voltage converter to produce a voltage output from the current through photodetector Q1. R1 is chosen to give a suitable voltage gain with the range of current available from Q1. Zener diode D1 provides a stable reference voltage for the circuit.

Amplifier A2 is used as comparator to determine whether A1's output voltage is above or below the threshold voltage set by potentiometer R4. If the output voltage of A1 is higher than the threshold voltage, corresponding to a high light level, the output of A2 goes to its positive limit. This turns on green LED D2 which indicates a diet beverage. R2 and R3 are chosen to provide hysteresis, giving a positive switching action to the comparator.

A3 is connected as an inverter. When the output of A2 is high, the output of A3 goes low, preventing red LED D3 from turning on. When the output of A2 is low, as when a sugar-sweetened beverage is detected, the output of A3 goes high, turning on D3 which indicates a sugar sweetened beverage.

The user presses the power button 13 to activate the device and dips the probe 16 into the liquid to be tested. The device immediately lights an indicator to display the result of the test. In the preferred embodiment of the device, a red light 14 indicates the presence of sugar and a green light 15 indicates the absence of sugar.

The electronic circuitry can include means for reducing the sensitivity of the device to ambient light, such as modulation or synchronous detection. The device may include a means to indicate low battery level. The device may include an audible alarm to alert the user when a beverage is found to contain sugar. The alarm may consist of a tone or other distinctive sound, or a voice saying, for example, "Sugar." The probe may be made retractable for protection while the device is being carried. It could slide or pivot out of the enclosure for use.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

I claim:

1. A device for discreetly determining if a beverage is sugar sweetened comprising:
   an enclosure;
   A unitary electronic circuit held by said enclosure, said unitary electronic circuit including an alarm;
   a battery connected to said electronic circuit;
   a light source connected to said battery, said light source emitting a beam of light;
   an elongated probe having a light receiving end and a faceted end, said elongated probe being fabricated from a transparent material and having a longitudinal axis extending from said light receiving end to said faceted end, said light source being positioned to shine a beam of light on said light receiving end of said probe and to transmit said beam of light along said elongated probe parallel to said longitudinal axis and said faceted end having at least two facets comprising an inclined face and a mirrored face, said inclined face being formed at an angle with respect to said longitudinal axis so that said beam of light is totally reflected when said inclined face is immersed a beverage comprising pure water, and further that said beam of light is transmitted through said inclined face when said inclined face is immersed in a beverage containing at least about six percent of dissolved sugar and said mirrored face being formed at an angle with respect to said longitudinal axis and to said inclined face so as to reflect so much of said beam of light which is reflected from said inclined face into said probe and to provide a reflected beam of light;
   a photodetector positioned to receive light from said reflected beam, said photodetector being connected to said electronic circuit and said electronic circuit including means to activate said alarm when said photodetector receives light from said reflected beam; and
   a plurality of light beam blocking elements extending through said elongated probe positioned on said longitudinal axis of said unitary elongated probe, said light beam blocking elements being oriented normal to said longitudinal axis.

2. The device for discreetly determining if a beverage is sugar sweetened of claim 1 wherein said alarm is at least one indicator light.

3. The device for discreetly determining if a beverage is sugar sweetened of claim 2 wherein said alarm comprises two indicator lights comprising a diet indicator light and a sugar indicating light and said electronic circuit further includes a power switch connected to turn on said light source and said circuit is configured to turn on said diet indicator light when said beam of light is reflected from said inclined face and to turn on said sugar indicator light when said beam of light is not reflected from said inclined face.

4. The device for discreetly determining if a beverage is sugar sweetened of claim 3 wherein said diet indicator light is green and said sugar indicator light is red.

5. The device for discreetly determining if a beverage is sugar sweetened of claim 1 wherein said elongated probe is held by said enclosure so that its light receiving end is within said enclosure and said faceted end extends outwardly from said enclosure.

6. The device for discreetly determining if a beverage is sugar sweetened of claim 1 wherein said plurality of light blocking elements include at least one notch formed inwardly from a side of said rectangular cross sectional shape.

7. The device for discreetly determining if a beverage is sugar sweetened of claim 6 wherein said probe includes two holes formed through said probe, a first hole being positioned between said notch and said faceted end and a second hole being positioned between said notch and said light receiving end.

8. The device for discreetly determining if a beverage is sugar sweetened of claim 1 wherein said plurality of light blocking elements includes at least two holes formed through said probe.

9. The device for discreetly determining if a beverage is sugar sweetened of claim 8 wherein said probe includes two holes formed through said probe.

10. The device for discreetly determining if a beverage is sugar sweetened of claim 1 wherein said photodetector is positioned adjacent said light receiving end.

11. A device for discreetly determining if a beverage is sugar sweetened comprising:

an electronic circuit including a battery and a light source which emits a beam of light;

an elongated probe having a unitary elongated body with a light receiving end for receiving said beam of light and transmitting said beam of light through said elongated body and said elongated body having a longitudinal axis, a faceted end, said faceted end including an inclined face being formed at an angle with respect to said longitudinal axis of said elongated probe so that said beam of light passed through said elongated body parallel to said longitudinal axis is totally reflected and produces a reflected beam from an inner face of said inclined face when said inclined face is immersed a beverage having a refractive index of pure water, and further that said beam of light is transmitted through said inclined face when said inclined face is immersed in a beverage having a refractive index of an aqueous solution containing at least about six percent of dissolved sugar;

means for reflecting said reflected beam to a photodetector;

a plurality of light beam blocking elements extending through said elongated probe positioned on said longitudinal axis of said unitary elongated probe, said light beam blocking elements being oriented normal to said longitudinal axis; and means for indicating when said photodetector is receiving said reflected beam whereby a user may dip the inclined face into a beverage and if the beverage has a refractive index about that of pure water, the beam of light will be reflected into said photodetector and said means for indicating will inform the user that the beverage does not contain sugar.

12. The device for discreetly determining if a beverage is sugar sweetened of claim 11 wherein said light source and said photodetector are position adjacent said light receiving end.

13. The device for discreetly determining if a beverage is sugar sweetened of claim 12 wherein said faceted end includes a mirrored face being formed at an angle with respect to said central axis and to said inclined face to reflect so much of said beam of light which is reflected from said inclined face rearwardly in said probe to said photodetector.

\* \* \* \* \*